US00PP08530P

United States Patent [19]

Young

[11] Patent Number: Plant 8,530

[45] Date of Patent: Jan. 4, 1994

[54] NANDINA DOMESTICA CV. "GRERAY"

[75] Inventor: Richard A. Young, El Campo, Tex.

[73] Assignee: Greenleaf Nursery Company, Park Hill, Okla.

[21] Appl. No.: 893,411

[22] Filed: Jun. 2, 1992

[51] Int. Cl.[5] ..... A01H 5/00

[52] U.S. Cl. ..... Plt./54.1

[58] Field of Search ..... Plt. 54.1

*Primary Examiner*—James R. Feyrer

*Attorney, Agent, or Firm*—Synnestvedt & Lechner

[57] ABSTRACT

A new variety of *Nandina domestica* having significant and improved characteristics not known to exist in either the variety "Harbour Dwarf" of which this new plant is a genetic mutant or the general species *Nandina domestica*. These characteristics include a symmetrical, densely mounding and compact form.

6 Drawing Sheets

BACKGROUND OF THE NEW PLANT

This invention relates to the discovery and asexual propagation of a new and distinct variety of *Nandina domestica* (a member of the Berberidacia family that is commonly known as "Heavenly Bamboo"). The new plant variety was discovered as a mutant of the *Nandina domestica nana* cultivar named "Harbour Dwarf" in a cultivated bed of "Harbour Dwarf" plants that were growing in the Greenleaf Nursery Company, El Campo, Tex. The new variety of Nandina domestica nana has been named "Greray".

The "Greray" mutant exhibited vastly different growing characteristics than those common to the "Harbour Dwarf" variety-particularly in that the "Greray" variety has a dwarf habit of growth when compared to the *Nandina domestica* progenitor "Heavenly Bamboo", but it is not as dwarf as its parent *Nandina domestica nana* "Harbour Dwarf". The new "Greray" variety is symmetrical, densely mounding and compact in form which differentiates and distinguishes it not only from its parent "Harbour Dwarf" and from its progenitor "Heavenly Bamboo", but also from related cultivars such as the variety called "Compacta". The new "Greray" cultivar is freely branching from basal and lateral buds and thus forms a tight compact globe. Its leaves are tripinnately compound.

Testing and evaluation has shown the "Greray" variety to be stable in its distinguishing characteristics over several succeeding generations upon asexual propagation by using shoot cuttings and by tissue culturing at a nursery in El Campo, Tex.

The "Greray" variety fully lives up to the "Heavenly Bamboo" common name often given to this family of plants. Orange hued new growth radiates crown-like upward while refreshing green mature growth extends horizontally to present a perky, full foliaged appearance. The refined texture of this plant is desirable for formal or casual settings. The fullness and controlled height of this dwarf nandina make it a prime choice when accent or foundation plantings are needed.

The accompanying drawings illustrate the new "Greray" variety in color as grown in a nursery in El Campo, Tex. and also enable comparing "Greray" to its progenitor "Heavenly Bamboo", to its parent "Harbour Dwarf", and to another related Nandina domestica cultivar known as "Compacta"; the photographs also show the coloration of new, semi-mature and mature foliage of the new "Greray" variety.

In FIG. 1:

FIG. 1-A is a color photograph of a mature, unpruned parent Nandina domestica "Harbour Dwarf".

FIG. 1-B is a color photograph of a mature, unpruned progenitor Nandina domestica "Heavenly Bamboo."

FIG. 1-C is a color photograph of another mature, unpruned Nandina domestica cultivar known as "Compacta."

FIG. 1-D is a color photograph of a 28 month old unpruned "Greray" nandina grown from softwood cuttings taken from the original mother.

Figure 1:
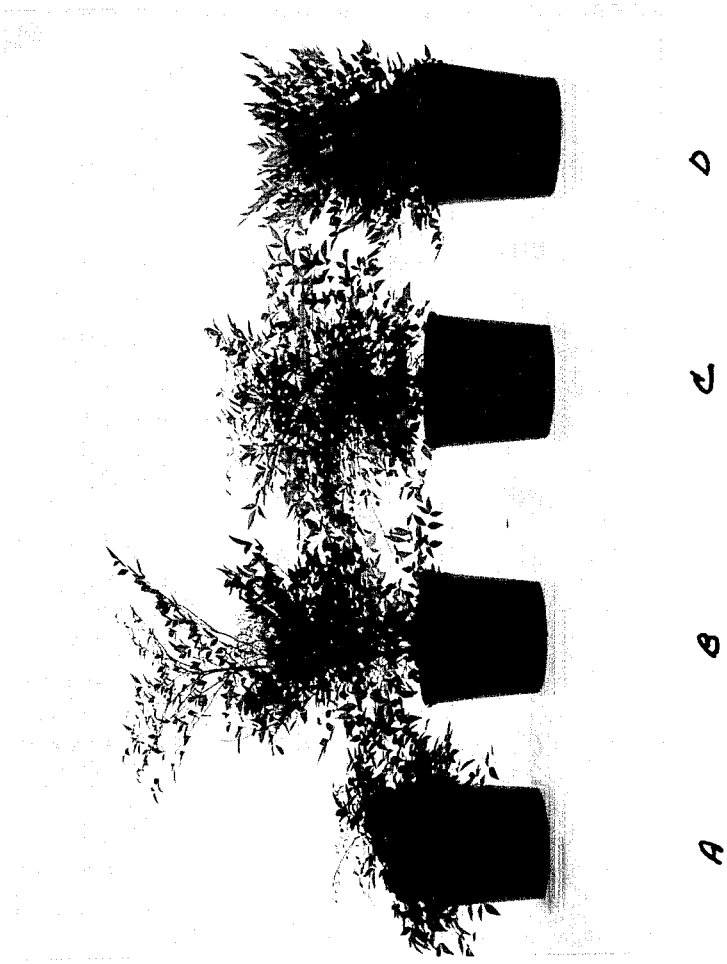
Figure 2:
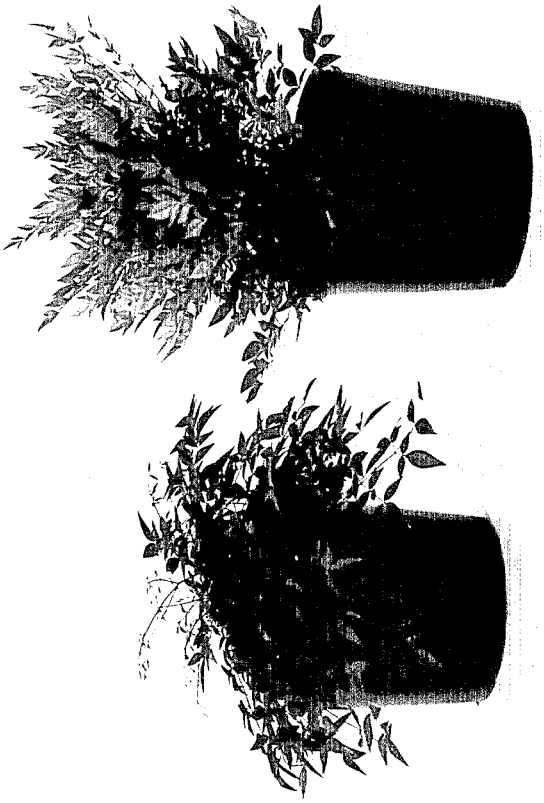
FIG. 2 is a color photograph of a mature, unpruned parent Nandina domestica "Harbour Dwarf" (on the left) and (on the right) the "Greray" plant of FIG. 1-D.
Figure 3:
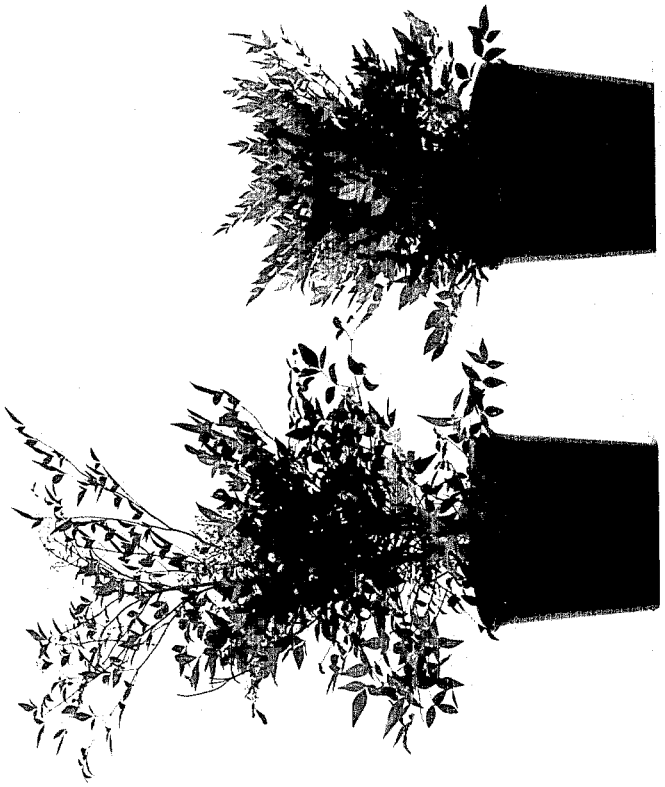
FIG. 3 is a color photograph of a mature, unpruned progenitor Nandina domestica "Heavenly bamboo" (on the left) and (on the right) the "Greray" planat of FIG. 1-D.
Figure 4:
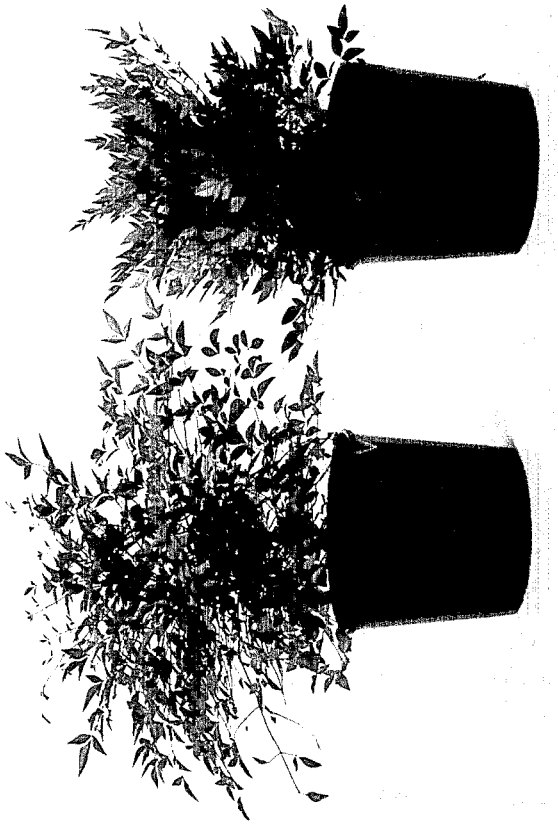
FIG. 4 is a color photograph of another mature, unpruned Nandina domestica cultivar known as "Compacta" (on the left) and (on the right) the "Greray" plant of FIG. 1-D.
Figure 5:
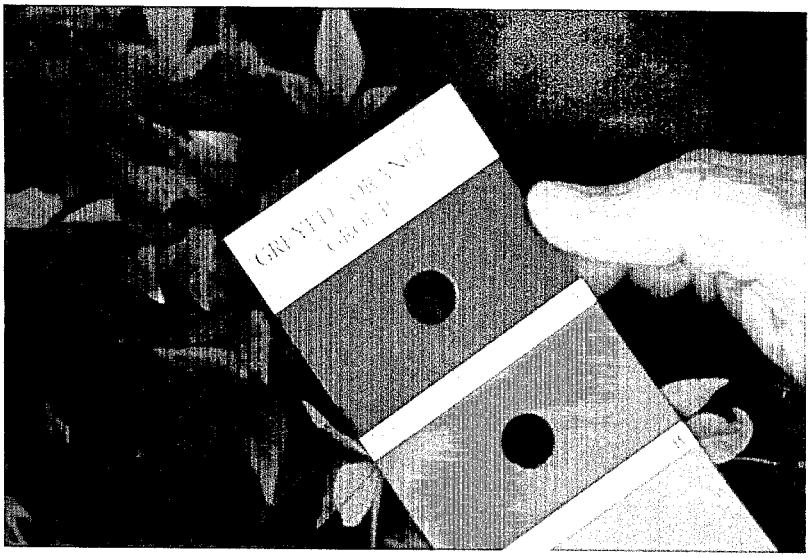
FIG. 5 is a color photograph of a close up of the new foliage of the "Greray" variety superimposed by the matching color card of the Greyed Orange group R.H.S. 166.
Figure 6:
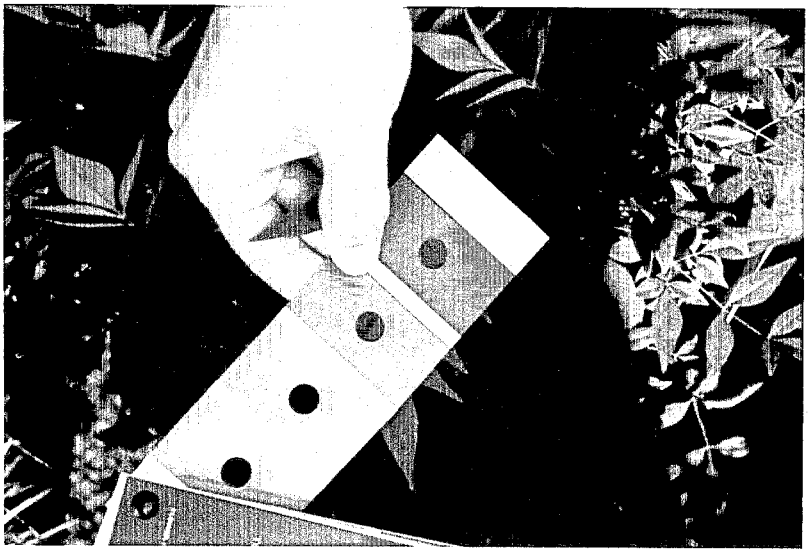
FIG. 6 is a color photograph of a close up of the semi-mature foliage of the "Greray" variety superimposed by the matching color card of the Yellow-Green group R.H.S. 146.
Figure 7:
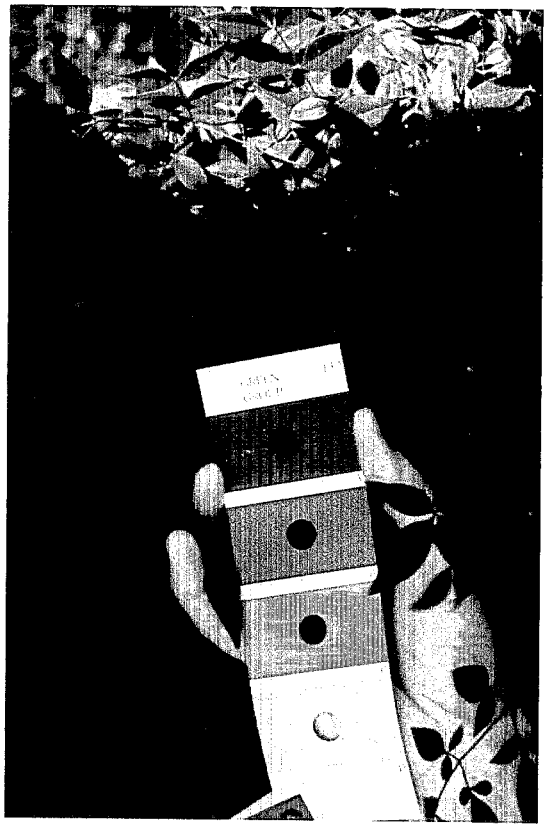
FIG. 7 is a color photograph of a close up of the mature foliage of the "Greray" variety superimposed by the matching color card of the Green group R.H.S. 139.

Throughout this specification, color names beginning with a small letter signify that the name of that color as used in common speech is aptly descriptive. Color names beginning with a capital letter designate values based on The R.H.S. Colour Chart published by The Royal Horticultural Society of London, England.

The descriptive matter which follows pertains to the "Greray" variety of Nandina domestica plants and related cultivars grown outdoors in El Campo, Tex., and is believed to apply to plants of the "Greray" variety grown in similar conditions of soil and climate elsewhere.

DETAILED PLANT DESCRIPTION

Name: *Nandina domestica nana* Greray

Parentage: A mutation of asexually propagated *Nandina domestica nana* "Harbour Dwarf".

Size: Ultimate mature height at 24–36 months will be 24–36".

Growth habit: Dwarf, symmetrical densely compact mound. The plant branches freely from basal and lateral buds.

Foliage:

*Arrangement.*—Alternate, tri-pinnately compound, evergreen.

*Size.*—20 cm to 23 cm (mature foliage).

*Shape* and *form.*—Leaflets are elliptic-lanceolate and ascending. Leaflets are apex and basal acute.

*Leaflet width.*—Varies between 8 mm and 17 mm.

*Leaflet length.*—Varies between 17 mm and 55 mm.

*Stem form.*—Upright.

Texture: Medium.

Flowers: Perfect flowers that are slightly pink in bud, turning white with yellow anthers; each flower is about ¼" to ⅜" across, borne in erect terminal panicles about 8–15" long; flowering occurs in April/May in southern temperate zones.

Color:

TABLE I

| | TOP SIDE OF LEAF | | |
|---|---|---|---|
| | GRERAY | MOON BAY | GULF-STREAM |
| New Foliage | Greyed-Orange 174 A | Yellow-Green 152 A | Greyed-Orange 174 A |
| Mature Foliage | Green 138 A | Yellow-Green 152 B | Yellow-Green 147 B |
| Old Foliage | Green 139 A | Yellow-Green 147 A | Green 139 A |

TABLE II

| | UNDER SIDE OF LEAF | | |
|---|---|---|---|
| | GRERAY | MOON BAY | GULF STREAM |
| New Foliage | Greyed-Orange 177 C | Greyed-Orange 177 D | Yellow-Green 148 B |
| Mature Foliage | Yellow-Green 146 B | Yellow-Green 148 C | Yellow-Green 148 B |
| Old Foliage | Greyed-Green 191 A | Yellow-Green 147 B | Green 138 A |

Climatic range: This plant has survived winter temperatures as low as 5° F. in trials in our Northeastern Oklahoma growing grounds which is somewhat indicative of its parentage which is hardy to Zone 6 USDA.

Table III below is a comparison of the *Nandina domestica nana* "Greray" with its parent "Harbour Dwarf" and with other related Nandina varieties, including "Compacta," "Heavenly Bamboo," "Moon Bay," "Gulf Stream" and "Lowboy."

TABLE III

| | GRERAY | HARBOUR DWARF |
|---|---|---|
| Size | 24"–36" at maturity | 18"–24" at maturity |
| Growth Habit | Dwarf, symmetrical, densely compact mound branches freely from basal and lateral buds. | Extremely dense, very dwarf form. |
| Foliage | Alternate, tri-pinn compound, evergreen. Leaflets are 17–15 mm long, and 8–17 mm wide. | Alternate, tri-pinn compound, evergreen. |
| Texture | Medium | Fine |
| Flowers | Perfect flowers that are slightly pink in bud turning white with yellow anthers, each flower is ¼" to ⅜" across, borne in erect terminal panicles 8–15" long. Flowering occurs in April/May in Southern temperate zones. Flowering is not as profuse as Nandina domestica, but is very similar to parent 'Harbour Dwarf'. | Perfect flowers that are slightly pink in bud turning white with yellow anthers, each flower is ¼" to ⅜" across, borne in erect terminal panicles 8–15" long. Flowering occurs in April/May in Southern temperate zones. |
| Fruit | None observed to date, but expect to see a few red berries set in the clustered flower heads. | Few small red berries in fall |

| | COMPACTA | HEAVENLY BAMBOO |
|---|---|---|
| Size | 5'–6' at maturity | 5'–6' at maturity |
| Growth Habit | More dense than parent, Heavenly Bamboo, with a more rhizonous habit of spreading. | Upright, generally unbranched, tends to open up its foliage density nearer the base exposing multiple canes or shoots. |
| Foliage | Alternate, twice or thrice compound with leaflets slightly smaller than Heavenly Bamboo (20–30 mm), evergreen. | Alternate, twice thrice compound, leaflets are 25–38 mm long, evergreen. |
| Texture | Medium | Medium |
| Flowers | Perfect flowers that are slightly pink in bud turning white with yellow anthers, each flower is ¼" to ⅜" across, borne in erect terminal panicles 8–15" long. Flowering occurs in April/May in Southern temperate zones. | Perfect flowers that are slightly pink in bud turning white with yellow anthers, each flower is ¼" to ⅜" across, borne in erect terminal panicles 8–15" long. Flowering occurs in April/May in Southern temperate zones. |
| Fruit | Clusters of small red berries in fall. | Clusters of small red berries in fall. |

| | MOON BAY | GULF STREAM |
|---|---|---|
| Size | 20" at maturity | 30" at maturity |
| Growth Habit | Dwarf, symmetrial, tight globular shape. Branches freely from basal and lateral buds developing multiple upright stems with ascending petiole, rachis, petiolule and leaflets. The cultivar does not appear to spread by rhizones. | Dwarf, symmetrical densely compact, solitary form. Branches freely from basal and lateral buds, giving a full round erect shape. |
| Foliage | Alternate, 2–3 pinn, | Alternate, tripin- |

TABLE III-continued

| | | |
|---|---|---|
| | compound, evergreen, leaflets 19 cm to 26.7 cm long, leaflet are elliptic-lanceloate, sharply concave, ascending. Leaflet 12.7–5.1 mm long by 6.4–12.7 mm wide. | nately compound, evergreen, leaflets are elliptic lanceolate, slightly concave, ascending leaflet, length varies between 13 mm and 51 mm. |
| Texture | Medium | Medium |
| Flowers | None observed | None observed |
| Fruit | None observed. | None observed. |

| | LOWBOY |
|---|---|
| Size | 24"–36" at maturity |
| Growth Habit | Stoloniferous; dense compact, mounded spreading habit. In Semmes, AL, there is more-or-less continuous growth from June to August. |

TABLE III-continued

| | |
|---|---|
| Foliage | 10"–16" long leaf, 16"–24" wide. leaflets are ½" to 2" long, 8"–12" wide. Tripinnately compound leaflets, subsessile, elliptic-lanceolate, cuneate, prominent midveins, secondary veins scarcely noticeable. Leaflets composed of up to 170, ½ to 2" long, one-half size of species. |
| Texture | Somewhat leathery |
| Flowers | Small white flowers in May and June |
| Fruit | Small red berry on 3–4 yr. old plants |

I claim:

1. The new and distinct variety of *Nandina domestica nana* called "Greray" as illustrated and described.

* * * * *